United States Patent
Freiman et al.

(10) Patent No.: US 12,051,202 B2
(45) Date of Patent: Jul. 30, 2024

(54) SPECTRAL IMAGING FFR

(71) Applicant: KONINKLIJKE PHILIPS N.V., Eindhoven (NL)

(72) Inventors: Mordechay Pinchas Freiman, Zichron-Yaakov (IL); Liran Goshen, Pardeds-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 16/498,730

(22) PCT Filed: Mar. 29, 2018

(86) PCT No.: PCT/EP2018/058078
§ 371 (c)(1),
(2) Date: Sep. 27, 2019

(87) PCT Pub. No.: WO2018/178239
PCT Pub. Date: Oct. 4, 2018

(65) Prior Publication Data
US 2020/0034968 A1    Jan. 30, 2020

Related U.S. Application Data

(60) Provisional application No. 62/479,670, filed on Mar. 31, 2017, provisional application No. 62/540,089, filed on Aug. 2, 2017.

(51) Int. Cl.
*G06T 7/00* (2017.01)
*G06T 7/12* (2017.01)
(Continued)

(52) U.S. Cl.
CPC ............. *G06T 7/0014* (2013.01); *G06T 7/12* (2017.01); *G06T 17/005* (2013.01); *G16H 30/40* (2018.01);
(Continued)

(58) Field of Classification Search
None
See application file for complete search history.

(56) References Cited

U.S. PATENT DOCUMENTS 7,968,853 B2    6/2011    Altman
7,983,382 B2    7/2011    Thomsen
(Continued)

FOREIGN PATENT DOCUMENTS

WO    WO2016001017 A1    1/2016
WO    WO2018050806 A1    3/2018

OTHER PUBLICATIONS

PCT International Search Report, International application No. PCT/EP2018/058078, Jun. 8, 2018.
(Continued)

*Primary Examiner* — Yanna Wu
(74) *Attorney, Agent, or Firm* — Larry Liberchuk

(57) ABSTRACT

A system (100) includes a computer readable storage medium (122) with computer executable instructions (124), including: a biophysical simulator component (126) configured to determine a fractional flow reserve index. The system further includes a processor (120) configured to execute the biophysical simulator component (126) to determine the fractional flow reserve index with spectral volumetric image data. The system further includes a display configured to display the determine fractional flow reserve index.

19 Claims, 2 Drawing Sheets

(51) Int. Cl.
G06T 17/00 (2006.01)
G16H 30/40 (2018.01)
G16H 50/50 (2018.01)

(52) U.S. Cl.
CPC ... *G16H 50/50* (2018.01); *G06T 2207/10081* (2013.01); *G06T 2207/30048* (2013.01); *G06T 2207/30101* (2013.01); *G06T 2207/30104* (2013.01); *G06T 2211/404* (2013.01)

(56) References Cited

U.S. PATENT DOCUMENTS

| | | | |
|---|---|---|---|
| 10,186,056 B2 | 1/2019 | Senzig | |
| 10,258,303 B2 | 4/2019 | Grass | |
| 10,769,780 B2 | 9/2020 | Freiman | |
| 2013/0108013 A1* | 5/2013 | Leng | A61B 6/032 378/19 |
| 2014/0005535 A1 | 1/2014 | Edic | |
| 2014/0187932 A1* | 7/2014 | Li | A61B 6/481 600/431 |
| 2015/0038860 A1* | 2/2015 | Fonte | A61B 6/5217 600/505 |
| 2015/0297161 A1 | 10/2015 | Grass | |
| 2016/0321803 A1 | 11/2016 | Lamash | |
| 2018/0032653 A1 | 2/2018 | Aben | |
| 2020/0375564 A1 | 12/2020 | Freiman | |

OTHER PUBLICATIONS

Freiman M. et al., "Learning an Optimal Database for Patch-Based Medical Image Segmentation: A Total-Variation Approach", Electrical Engineering and Systems Science, Image and Video Processing, Jun. 2019.

Fahmi R. At El., "Dynamic Myocardial Perfusion in a Porcine Balloon-induced Ischemia Model using a Prototype Spectral Detector CT", Medical Imaging 2015: Biomedical Applications in Molecular, Structural, and Functional Imaging, Proc. of SPIE vol. 9417, Feb. 2015.

Freiman et al., "Automatic Coronary Lumen Segmentation with Partial Volume Modeling Improves Lesions' Hemodynamic Significance Assessment," Progress in Biomedical Optics and Imaging—Proceedings of SPIE, vol. 9784, 2016.

Vorobtsova N. et al., "Effects of Vessel Tortuosity on Coronary Hemodynamics: An Idealized and Patient-Specific Computational Study," Annals of Biomedical Engineering, vol. 44, No. 7, pp. 2228-2239, Jun. 8, 2015.

Lee M.S et al., "Myocardial Bridging: An Up-to-Date Review", The Journal of Invasive Cardiology, vol. 27, No. 11, pp. 521-8, Nov. 2015.

Meijboom W. B. et al., "Comprehensive Assessment of Coronary Artery Stenoses. Computed Tomography Coronary Angiography Versus Conventional Coronary Angiography and Correlation With Fractional Flow Reserve in Patients With Stable Angina," Journal of the American College of Cardiology., vol. 52, No. 8, pp. 636-643, Oct. 18, 2007.

Coenen A. et al., "Fractional Flow Reserve Computed from Non-invasive CT Angiography Data: Diagnostic Performance of an On-Site Clinician-Operated Computational Fluid Dynamics Algorithm," Radiology, vol. 274, No. 3, pp. 674-683, Mar. 2015.

Norgaard B. L. et al., "Diagnostic Performance of Non-Invasive Fractional Flow Reserve Derived from Coronary CT Angiography in Suspected Coronary Artery Disease: The NXT trial.," Journal of the American College of Cardiology, vol. 63, No. 12, pp. 1145-1155, Oct. 18, 2013.

Nickisch H. et al., "Learning Patient-Specific Lumped Models for Interactive Coronary Blood Flow Simulations," in Medical Image Computing and Computer-Assisted Intervention—MICCAI 2015: 18th International Conference, LNCS, vol. 9350, pp. 433-441, Oct. 2015.

Murray C. J. L. et al., "Global, Regional, and National Age-Sex Specific All-Cause and Cause-Specific Mortality for 240 Causes of Death, 1990-2013: A Systematic Analysis for the Global Burden of Disease Study 2013," GBD 2015 Mortality and Causes of Death Collaborators, Lancet, vol. 385, No. 9963, pp. 117-171, Dec. 18, 2014.

Danad I. et al., "Dual-Energy Computed Tomography for Detection of Coronary Artery Disease", Expert Rev. Cardiovasc. Ther., vol. 13, No. 12, pp. 1345-1356, Dec. 2015.

Williams M.C. et al., "CT Coronary Angiography in Patients with Suspected Angina Due to Coronary Heart Disease (SCOT-HEART): An Open-Label, Parallel-Group, Multicentre Trial," Lancet, vol. 385, No. 9985, pp. 2383-2391, Mar. 15, 2015.

Lugauer F. et al., "Precise Lumen Segmentation in Coronary Computed Tomography Angiography," International MICCAI Workshop on Medical Computer Vision MCV 2014: Medical Computer Vision: Algorithms for Big Data, 2014, vol. 8848, pp. 137-147.

Wustmann K. et al., "Is There Functional Collateral Flow During Vascular Occlusion in Angiographically Normal Coronary Arteries?", Circulation, vol. 107, No. 17, pp. 2213-2220, Nov. 27, 2002.

* cited by examiner

SPECTRAL IMAGING FFR

FIELD OF THE INVENTION

The following generally relates to spectral imaging and more particularly to determining fractional flow reserve (FFR) estimates from spectral image data, and is described with particular application to computed tomography (CT).

BACKGROUND OF THE INVENTION

Fractional flow reserve (FFR) is an invasive measure in the catheterization laboratory (Cath Lab) to quantify, via an FFR index, the hemodynamic significance of a coronary lesion due to calcified or soft plaque. The index indicates the functional severity of a coronary stenosis that is calculated from pressure measurements made during coronary arteriography and is defined as the distal blood pressure (behind a stenosis) relative to the proximal pressure (close to the ostium) under hyperemic conditions. That is, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure.

The FFR invasive procedure requires insertion of a catheter into the femoral or radial arteries and advancement of the catheter to the stenosis where a sensor at the tip of the catheter senses pressure, temperature, and flow across the stenosis, during conditions promoted by various agents that effect vessel geometry, compliance and resistance, and/or other characteristics. FFR-CT is non-invasive imaging approach to estimate an FFR index from CT image data of the heart (e.g., from coronary computed tomography angiography, CCTA) through computational fluid dynamic (CFD) simulations in which blood flow and pressure through the coronaries are simulated. This includes using CCTA image data to derive a geometrical model of the coronary tree, extract features therefrom, and determine boundary conditions from the features for the simulation.

Unfortunately, CCTA image data can be limited in accurately characterizing underlying anatomy and physiology of a patient. An example of such a limitation is over-estimating of myocardial perfusion deficit, e.g., due to beam hardening. Another example of such a limitation is underestimating of a lumen radius, e.g., due to calcium blooming.

SUMMARY OF THE INVENTION

Aspects described herein address the above-referenced problems and others.

Described herein is an approach to enhance fractional flow reserve (FFR) estimates from coronary computed tomography angiography (CCTA) by utilizing spectral volumetric image data (e.g., CT) results to characterize the underlying anatomy and to assign boundary conditions to the simulation. The approach uses spectral image analysis applied to the spectral volumetric image data to derive an accurate patient-specific 3-D anatomical model of the coronary tree, and utilizes a statistical model to describe implicitly the complex underlying hyperemic physiological processes from the spectral CT data. The model implicitly accounts for potential biases in flow simulation based upon non-spectral CCTA data, e.g., by providing more detailed and accurate characterization of the underlying anatomy and physiology to derive from the boundary conditions for the simulation.

In one aspect, a system includes a computer readable storage medium with computer executable instructions, including: a biophysical simulator component configured to determine a fractional flow reserve index. The system further includes a processor configured to execute the biophysical simulator component to determine the fractional flow reserve index with spectral volumetric image data. The system further includes a display configured to display the determine fractional flow reserve index.

In another aspect, a computer readable medium is encoded with computer executable instructions which when executed by a processor causes the processor to: receive spectral volumetric image data, process the spectral volumetric image data to determine a fractional flow reserve index, and visually present the fractional flow reserve index.

In another aspect, a method includes receiving spectral volumetric image data, processing the spectral volumetric image data to determine a fractional flow reserve index, and visually presenting the fractional flow reserve index.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
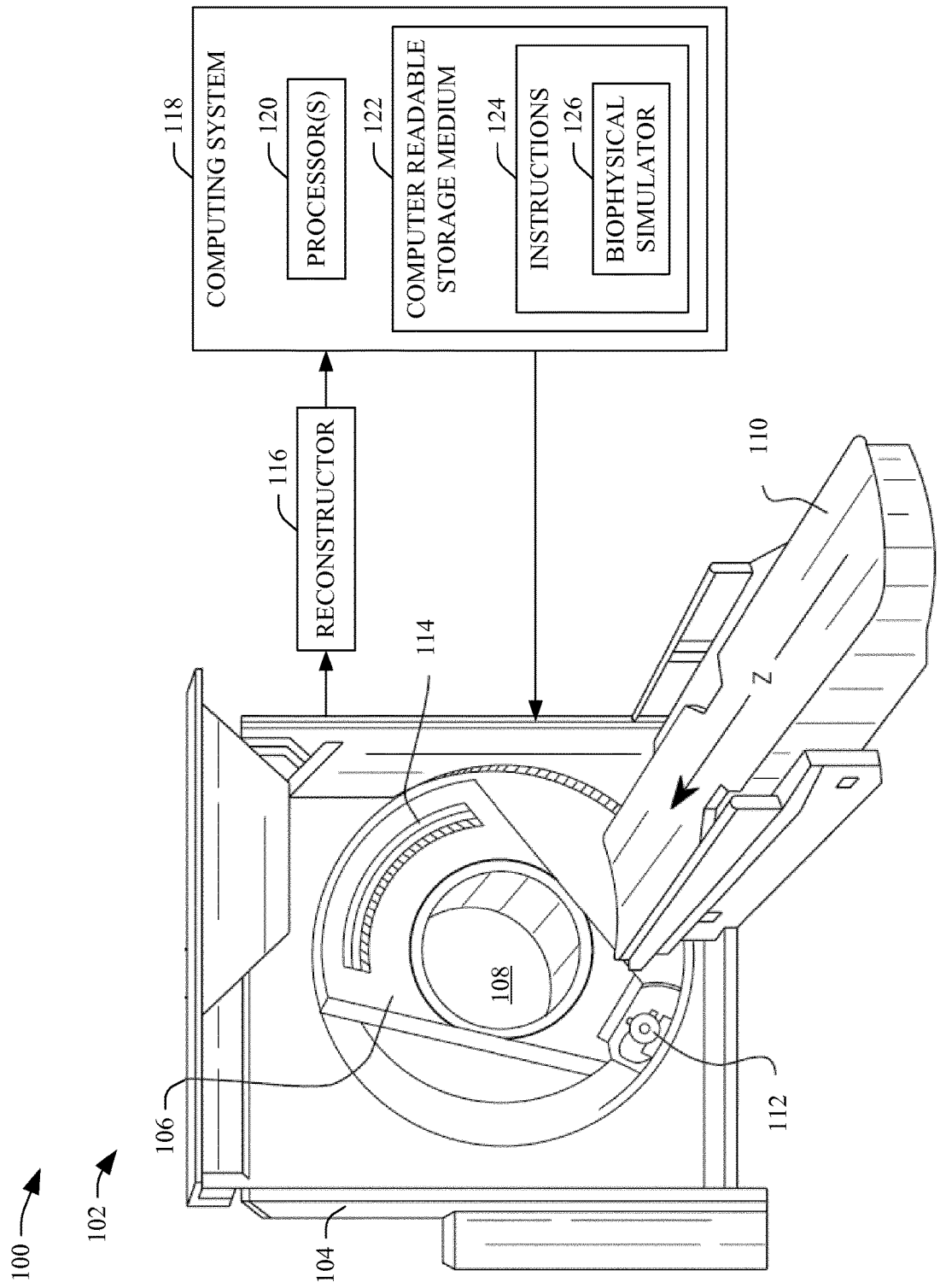
FIG. 1 schematically illustrates a system, including a computing system, with a biophysical simulator, and an imaging system.

FIG. 1 schematically illustrates a system 100 including an imaging system 102 such as a CT scanner configured for spectral (multi-energy) imaging. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. In one instance, the radiation source 112 includes a single broad spectrum x-ray tube. In another instance, the radiation source 112 includes a single x-ray tube configured to switch between at least two different emission voltages (e.g., 80 kVp and 140 kVp) during scanning. In yet another instance, the radiation source 112 includes two or more x-ray tubes configured to emit radiation having different mean spectra. In still another instance, the radiation source 112 includes a combination thereof.

A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof. Where the radiation source 112 includes a single broad spectrum x-ray tube, the radiation sensitive detector array 114 includes energy-resolving detectors (e.g., direct conversion photon counting detectors, at least two sets of scintillators with different spectral sensitivities (multi-layer), etc.). With kVp switching and multi-tube configurations, the detector array 114 can include single layer detectors, direct conversion photon counting detectors, and/or multi-layer detectors. The direct conversion photon counting detectors may include a conversion material such as CdTe, CdZnTe, Si, Ge, GaAs, or other direct conversion material. An example of a multi-layer detector includes a double decker detector such as the double decker detector described in U.S. Pat. No. 7,968,853 B2, filed Apr. 10, 2006, and entitled "Double Decker Detector for Spectral CT," the entirety of which is incorporated herein by reference.

A reconstructor 116 receives spectral projection data from the detector array 114 and reconstructs spectral volumetric image data such as spectral CCTA image data, a high-energy image, a low energy image, a photoelectric image, a Compton scatter image, an iodine image, a calcium image, a virtual non-contrast image, a bone image, a soft tissue image, and/or other basis material images. The reconstructor 116 can also reconstruct non-spectral volumetric image data, e.g., by combining spectral projection data and/or spectral volumetric image data. Generally, the spectral projection data and/or spectral volumetric image data will include data for at least two different energies and/or energy ranges.

A computing system 118 serves as an operator console. The console 118 includes a human readable output device such as a monitor and an input device such as a keyboard, mouse, etc. Software resident on the console 118 allows the operator to interact with and/or operate the scanner 102 via a graphical user interface (GUI) or otherwise. The console 118 further includes a processor 120 (e.g., a microprocessor, a controller, a central processing unit, etc.) and a computer readable storage medium 122, which excludes non-transitory medium, and includes transitory medium such as a physical memory device, etc. The computer readable storage medium 122 includes instructions 124 for at least a biophysical simulator 126. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another computing system, which is separate from the computing system 118.

The biophysical simulator 126 is configured to process at least the spectral volumetric image data generated by the reconstructor 116 and/or other imaging system to perform a biophysical simulation. With respect to FFR, the biophysical simulator determines an FFR index therefrom. As described in greater detail below, the biophysical simulator 126 determines a patient-specific 3-D anatomical model of the coronary tree from the spectral volumetric image data, extracts features therefrom, determines boundary conditions from the extracted features, and uses the spectrally determined boundary conditions for flow simulation and FRR index determination. In one instance, processing the spectral volumetric image data (relative to processing non-spectral volumetric image data) provides accurate and precise characterization of underlying anatomy and physiology of a patient. For example, the approach described herein can mitigate over-estimating of myocardial perfusion deficit due to beam hardening and/or underestimating of a lumen radius due to calcium blooming, relative to a configuration in which non-spectral volumetric image data is processed by the biophysical simulator 126.

Figure 2:
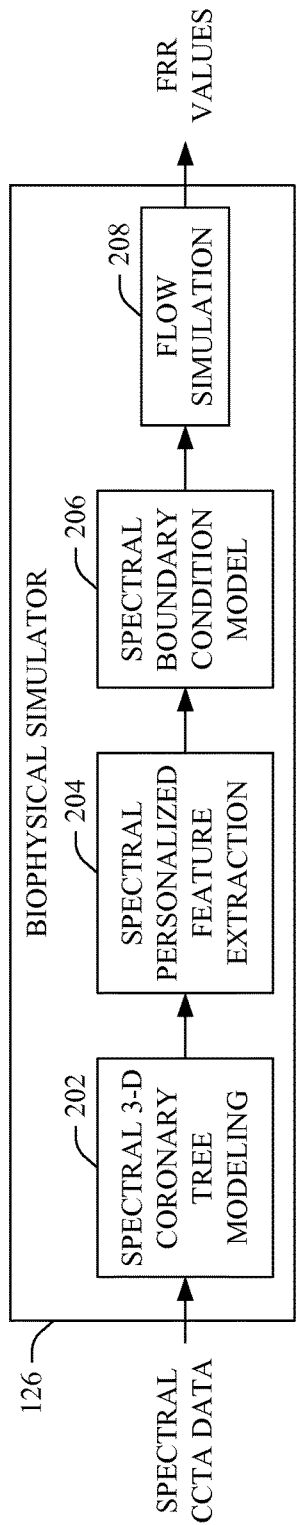
FIG. 2 schematically illustrates an example of the biophysical simulator.

FIG. 2 schematically illustrates an example of the biophysical simulator 126.

A 3-D coronary tree modeling component 202 receives and processes at least spectral volumetric image data (e.g., from the imaging system 102 and/or other imaging system) to generate a 3-D anatomical model of the coronary arteries. In one instance, patient demographics and/or other information is also used as input. The 3-D coronary tree modeling component 202 employs automatic and/or interactive segmentation tools to generate a 3-D anatomical model of the coronary arteries. An example of such a tool is described in Freiman, et al., "Automatic coronary lumen segmentation with partial volume modeling improves lesions' hemodynamic significance assessment," in Progress in Biomedical Optics and Imaging—Proceedings of SPIE, 2016, vol. 9784. The 3-D coronary tree modeling component 202 leverages the spectral volumetric image data to enhance the segmentation.

Examples of utilization of spectral data to enhance the segmentation include but not are limited to: (1) using different spectral results to determine a presence of different components of the coronary tree anatomy, e.g., use of an iodine map to determine the presence of a lumen, and virtual non-contrast image or z-effective map to determine a presence of calcified plaque; (2) using different mono-energetic images to find the boundary between different components rather than a single non-spectral image for the entire segmentation task, e.g., use of low mono-energetic images to define the boundary between lumen and soft-plaque, and high mono-energetic images to separate between calcified plaque and iodine in the lumen; and (3) using a spectrally enabled regularization to improve segmentation quality.

Examples of regularization include but are not limited to: (1) regularization over the different spectral results; and (2) regularization over the materials domain. The following provides an example in which spectral information is incorporated into an automatic coronary tree segmentation framework. In this example, the coronary lumen segmentation is formulated as a maximum a posterior estimation problem involving two terms: (1) a spectral data term; and (2) a spectral regularization term. It is to be appreciated that other formulations are contemplated herein, and the below formulation is not limiting.

The spectral data term represents a likelihood that each 3-D point belongs to one of the following classes: coronary lumen, calcified plaque, soft plaque, or background. An example of a spectral data term is shown in Equation 1:

$$\varphi_c(x,c_i) = Pr(f_{SCT}(x) \in c_i),$$ Equation 1:

where x is a 3-D point, $c_i$ is an ith class to be assigned to x, $Pr(\ )$ represents a probability, $f_{SCT}(x)$ extracts spectrally-enabled features from the spectral volumetric image data, e.g., iodine and calcium maps, and $Pr(f_{SCT}(x) \in c_i)$ represents a statistical model that describes a relationship between spectral features and the different classes.

The spectral regularization term penalizes neighboring points assigned to different classes (e.g., lumen/background). A general example of a regularization term is shown in Equation 2:

$$w(x_1,x_2) = Pr(x_1 \in c_1 \wedge x_2 \notin c_1).$$ Equation 2:

An example of a spectral regularization term or a spectrally enabled regularization term is shown in Equation 3:

$$\varphi_c(x, c_i) = Pr(x_1 \in c_1 \wedge x_2 \notin c_1) = \exp\left(-\frac{(f_s(x_1) - f_s(x_2))^2}{\sigma_s^2}\right),$$ Equation 3 where $f_s(x)$ is a feature-vector derived at point x from the spectral volumetric data, and $\sigma_s^2$ is an expected in-class variance over the spectral feature-vectors.

A personal feature extraction component 204 extracts features from the spectral volumetric image data and/or the 3-D coronary tree that are quantities related to the coronary blood flow. Examples include, but are not limited to: (1) spectral anatomical features, where the anatomy is detected, segmented and classified using spectral results, e.g., monoenergetic images, a calcium map with no soft tissue, a calcium map with no iodine, etc.; (2) spectral plaque features plaque, where the plaque is detected, segmented and classified using spectral results, e.g., a calcium map with no soft tissue, a calcium map with no iodine, etc.; (3) spectral myocardium deficits, where the myocardium deficits are detect, segment and assessed using spectral results, e.g., iodine map; (4) spectral collateral flow, where the collateral flow estimate is enhanced by spectral results, e.g., iodine map, and/or (5) other features.

A boundary condition parametric model component 206 determines an adjustable boundary condition parametric model from the features extracted from the spectral volumetric image data. There are a number of relations between the microvascular resistance and the anatomical and physiological features. Patent applications EP14174891.3 and U.S. 62/251,417 describe examples of some of the features related to the microvascular resistance, including the coronary outlet cross-sectional area, among others. Both EP14174891.3 and U.S. 62/251,417 are incorporated herein by reference in their entireties.

The boundary condition parametric model component 206, in one instance, can consider different, similar, parametric relations, including, e.g., weighted linear sum or weighted non-linear sum of the different effects. The following provides non-limiting examples.

In this example, the resistance is modeled as a function of the coronary outlet cross sectional area. An example for the relation between flows in the vessel and its branch with respect to its diameters is discussed in Vorobtsova et al., "Effects of Vessel Tortuosity on Coronary Hemodynamics: An Idealized and Patient-Specific Computational Study," Ann. Biomed. Eng., vol. 44, no. 7, pp. 2228-2239, 2016. As example is shown in Equation 4:

$$R_i = R_0 \cdot \frac{r_{in}^{\frac{1}{3}} \cdot \rho_{blood} \cdot r_{out,i}^{-\frac{7}{3}}}{\pi} \left[ \frac{g}{cm^4 \cdot s} \right], \qquad \text{Equation 4}$$

where $R_0$ represents a base overall resistance of the microvascular bed, $r_{in}$ represents an inlet diameter, $r_{out,i}$ represents an outlet diameter, and $\rho_{blood}$ represents blood viscosity. In this model, the base resistance scales directly with the inlet diameter and inversely with the outlet diameter to get the outlet resistance that is assigned at each coronary outlet.

An effective radius can be calculated from a cross-sectional area (CSA) shown in Equation 5:

$$r = \sqrt{\frac{CSA}{\pi}}. \qquad \text{Equation 5}$$

The base resistance can be found by machine-learning where a set of training data with invasively measured FFR values ($FFR_{GT}$, where GT=gold truth) is used to find an $R_0$ that maximizes the FFR-CT based classifier performance, as shown in Equation 6:

$$\widehat{R_0} = \underset{R_0}{\arg\max} \; AUC(FFR_{CT}(R_0, r_{in}, r_{out,i}), FFR_{GT}). \qquad \text{Equation 6}$$

The boundary condition parametric model component 206, in one instance, uses the Equation 7, which adjusts the overall resistance according to the patient-specific properties described above:

$$R_i = R_0 \cdot f(\text{patient\_spectral\_features}) \cdot \frac{r_{in}^{\frac{1}{3}} \cdot \rho_{blood} \cdot r_{out,i}^{-\frac{7}{3}}}{\pi} \left[ \frac{g}{cm^4 \cdot s} \right], \qquad \text{Equation 7}$$

where $f(\text{patient\_spectral\_features}): R^n \to R$ is a personalization function that relates the patient-specific spectral features described above to the patient's blood flow boundary conditions.

The following provides some examples of personalization, including anatomical personalization, spectral plaque morphological personalization, spectral perfusion deficit personalization, and spectral collateral flow personalization. The personalization may include one or more of these and/or other personalization.

Anatomical Personalization.

When considering a spectrally determined coronary tree inlet radius (rs) as a feature for flow simulation personalization, the term $f(\text{patient\_spectral\_features})$ can be written as shown in Equation 8:

$$f(\text{patient\_spectral\_features}) = \left( \min\left(2, \frac{A_0}{rs_{in}^2}\right) \right)^q, \qquad \text{Equation 8}$$

where patient_spectral_features={$rs_{in}$}, $A_0$ is a normalization factor, and q is an indicator to control whether the boundary conditions are personalized according to the inlet radius (q=1) or not (q=0).

Additional anatomical features that can be included are level of coronary tortuosity, which can influence the flow of blood through the coronary artery due to constriction of the artery while the heart muscle squeezes (discussed in Vorobtsova et al., "Effects of Vessel Tortuosity on Coronary Hemodynamics: An Idealized and Patient-Specific Computational Study," Ann. Biomed. Eng., vol. 44, no. 7, pp. 2228-2239, 2016) and presence and length of myocardial bridge associated with elastin degeneration, which may imply increased coronary stiffness (discussed in Lee, et al., "Myocardial Bridging: An Up-to-Date Review," J. Invasive Cardiol., vol. 27, no. 11, pp. 521-8, 2015).

An overall personalized model parameters $R_0$, $A_0$ can be found by machine-learning where a set of training data with invasively measured FFR values ($FFR_{GT}$) is used to find a $R_0$, $A_0$ that maximizes the FFR-CT based classifier performance, as shown in Equation 9:

$$\widehat{R_0, A_0} = \underset{R_0, A_0}{\arg\max} \; AUC(FFR_{CT}(R_0, A_0, r_{in}, r_{out,i}), FFR_{GT}), \qquad \text{Equation 9}$$

where AUC represents the area under the receiver operating curve.

Spectral Plaque Morphological Personalization.

When considering the spectrally determined plaque morphology, the patient_spectral_features∈ $R^n$ is a feature vector describing plaque morphology features. These features can include the total plaque volume, the calcified plaque volume, the non-calcified plaque volume, the number of calcified spots in the tree, the total length of the plaque, etc. The personalization function ƒ(patient_spectral_features): $R^n \rightarrow R$ describes a relationship between the plaque morphology features and the scaling of the global resistance. The function internal weighting parameters ($f_{internal}$) can be found using an optimization technique shown in Equation 10:

$$R_0, f\_internal = \underset{R_0, f_{internal}}{\arg\max} \ AUC($$

Equation 10

$$FFR_{CT}(R_0, f_{internal}, \text{patient\_spectral\_featuers}, r_{out,i}), FFR_{GT}).$$

Spectral Perfusion Deficit Personalization.

When considering the spectrally enabled perfusion deficit at the myocardium as the feature to personalize the boundary condition upon, the patient_spectral_features∈ $R^n$ is a feature vector that describes spectrally determined perfusion deficit features. These features can be derived from spectral volumetric imaging data and can include the iodine map, beam-hardening corrected mono energetic images, etc. The personalization function ƒ(patient_spectral_features): $R^n \rightarrow R$ describes a relationship between the spectrally enabled perfusion deficit features and the scaling of the global resistance. The function internal weighting parameters can be found using an optimization technique similar to the one described in Equation 10.

Spectral Collateral Flow Personalization

Collateral flow is an auto-regulation mechanism used by the body to prevent ischemia in case of coronary stenosis by creating new arterioles that support collateral blood flow to the potentially ischemic region. The literature indicates that even in the absence of obstructive CAD or in entirely normal hearts, there has been collateral flow to a briefly occluded coronary artery sufficient to prevent ECG signs of myocardial ischemia in 20-25% of the population studied. The boundary condition parametric model component 206, in one instance, takes into account collateral flow in boundary condition models for FFR-CT simulation in the estimation of the FFR.

Due to the small diameter of the collateral arterioles, CCTA cannot directly depict the presence of collateral arterioles that support collateral blood flow. As a result, boundary condition models do not account for the presence of collateral flow, which may cause inaccurate estimation of the FFR values. In U.S. 62/251,417, which is incorporated herein by reference in its entirety, the collateral flow estimate from non-spectral CT to adjust the boundary condition (BC) model for flow simulation. The approach, in one instance, using an indirect technique to estimate collateral flow based on the coronary intensity profile was used to quantify the presence of collateral flow.

The boundary condition parametric model component 206, in one instance, uses the spectral volumetric image data to quantify the collateral flow. Assessment of collateral flow from the spectral CT data can be done for example by the following steps: (1) determining the coronary tree, including lumen and wall, with the 3-D coronary tree modeling component 202, as described herein; (2) determining a myocardium feeding territory of each coronary, e.g., by using Voronoi diagrams; and (3) quantifying a presence of collateral flow, e.g., by determining additional iodine-related enhancement in the feeding territory of a coronary artery that is not related to the flow through the coronary.

The boundary condition parametric model component 206 employs the spectrally enabled collateral flow as the feature to personalize the boundary condition by defining the term patient_spectral_features∈ $R^n$ (Equation 8) as a feature vector describes spectrally determined collateral flow features.

A flow simulation component 208 performs a flow simulation with the boundary condition model. Flow simulations can be done using a 3-D computational fluid dynamics (CFD) approach and/or a reduced-order approach, such as the approached described by Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. In one instance, this component performs the flow simulation to estimate the hemodynamic significance of a coronary lesion using the 3-D anatomical model and the personalized boundary condition model.

The approach described herein, in one instance, provides an improved noninvasive, accurate, objective assessment of coronary lesions hemodynamic significance by means of fractional flow reserve (FFR). The coronary flow simulation is based on data from spectral volumetric image data, which, relative to non-spectral volumetric image data, can, in one instance, better characterize the anatomy and physiology of the patient and has the potential to provide more accurate FFR estimates.

Figure 3:
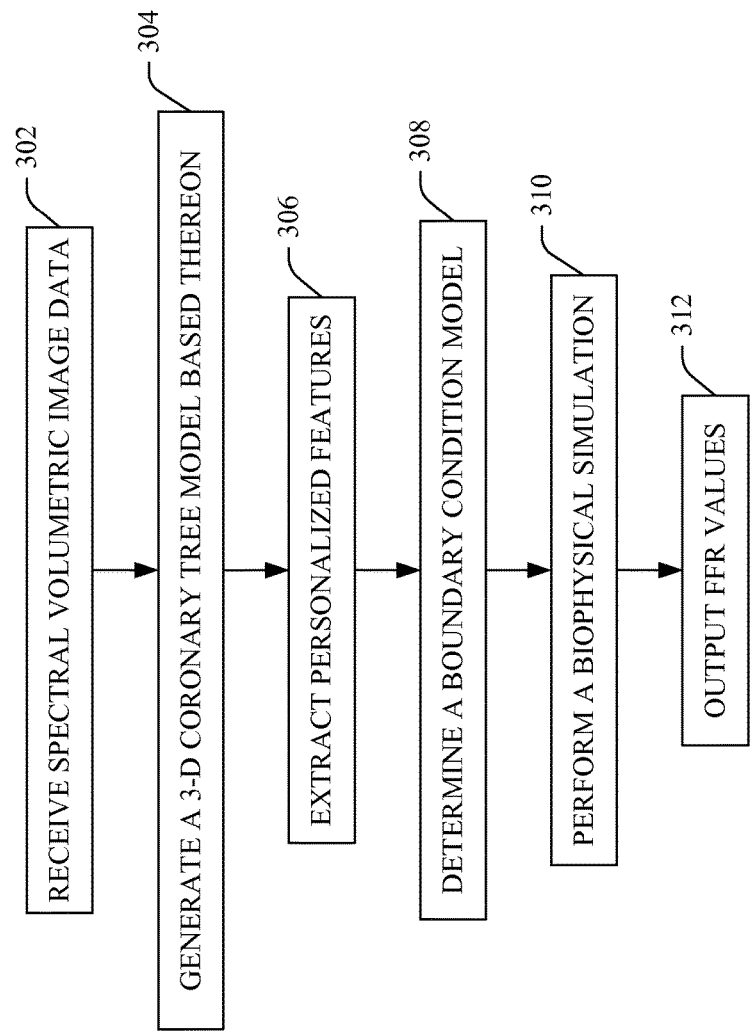
FIG. 3 illustrates an example method in accordance with an embodiment herein.

FIG. 3 illustrates an example method in accordance with an embodiment described herein.

The ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 302, spectral volumetric image data is received, as described herein and/or otherwise.

At 304, a 3-D coronary model is generated based on the spectral volumetric image data, as described herein and/or otherwise.

At 306, personalized features are extracted, as described herein and/or otherwise.

At 308, a boundary condition model is determined, as described herein and/or otherwise.

At 310, a biophysical simulation is performed.

At 312, the computed FFR values are output.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

Described herein is an approach to enhance fractional flow reserve (FFR) estimates from Coronary Computed Tomography Angiography (CCTA) by utilizing spectral CT results to characterize the underlying anatomy and to assign boundary conditions to the simulation. The new approach uses spectral-CT image analysis methods applied to the spectral CT data to derive a more accurate patient-specific 3D anatomical model of the coronary tree, and utilize a statistical model to describe implicitly the complex underlying hyperemic physiological processes from the spectral CT data.

This model assigns personalized boundary conditions using spectrally derived features of the cardiac system, including: 1) spectrally enhanced geometrical features such as cardiac and coronary tree radiuses, number and level of branches, presence of coronary bridge and level of tortuosity, 2) spectrally enhanced plaque characteristics, and; 3) spectrally enhanced physiological features such as myocardial perfusion deficit and collateral flow, rather than applying 3D anatomy and a boundary condition model derived from conventional CCTA data.

The model implicitly accounts for potential biases in flow simulation based upon conventional CCTA data, by providing more detailed and accurate characterization of the underlying anatomy and physiology to derive from the boundary conditions for the simulation. Previously suggested boundary condition models derived from conventional CT data are subjected to various artifacts, including beam hardening, calcium blooming, among others which may introduce bias in characterizing the exact underling anatomical and physiological boundary condition for the simulation While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system, comprising:
a memory that stores a plurality of instructions that include a biophysical simulator component configured to determine a fractional flow reserve (FFR) index;
a processor configured to execute the biophysical simulator component to:
segment a 3-D anatomical model of coronary arteries from spectral volumetric image data by 1) using at least one high mono-energetic diagnostic image for a first set of different anatomies or materials to locate boundaries in the first set among the different anatomies or materials, and 2) using at least one low mono-energetic diagnostic image for a second set of the different anatomies or materials to locate boundaries in the second set among the different anatomies or materials; and
determine the FFR index based on the 3-D anatomical model of coronary arteries; and
a display configured to display the FFR index.

2. The system of claim 1, wherein the biophysical simulator component comprises a spectral coronary tree modeling component configured to locate a presence of anatomy of interest in a spectral image for the 3-D anatomical model of the coronary arteries.

3. The system of claim 1, wherein the biophysical simulator component comprises a spectral coronary tree modeling component configured to use different mono-energetic images to locate a boundary between different anatomy of interest in the spectral volumetric image data.

4. The system of claim 1, wherein the biophysical simulator component comprises a spectral coronary tree modeling component configured to employ a spectrally enabled regularization over different spectral results or a materials domain.

5. The system of claim 1, wherein the biophysical simulator component further includes a spectral personalized feature extraction component.

6. The system of claim 5, wherein the spectral personalized feature extraction component extracts a feature from a group of features including: an anatomical feature, a plaque feature, a myocardium deficit feature, and a collateral flow feature from at least one of the 3-D anatomical model of the coronary arteries and the spectral volumetric image data.

7. The system of claim 5, wherein the spectral personalized feature extraction component extracts an anatomical feature by detecting, segmenting and classifying anatomy using a spectral image.

8. The system of claim 1, wherein the biophysical simulator component further includes a spectral boundary condition parametric model component configured to determine an adjustable boundary condition parametric model from the spectrally extracted features.

9. The system of claim 8, wherein the adjustable boundary condition parametric model component models a resistance as a function of a coronary outlet cross sectional area and a personalization term.

10. The system of claim 9, wherein the personalization term includes a term from a group including: an anatomical personalization, a spectral plaque morphological personalization, a spectral perfusion deficit personalization, and a spectral collateral flow personalization.

11. A non-transitory computer readable medium encoded with computer executable instructions which, when executed by a processor, cause the processor to:
receive spectral volumetric image data;
process the spectral volumetric image data to:
segment a 3-D anatomical model of coronary arteries from the spectral volumetric image data by 1) using at least one high mono-energetic diagnostic image for a first set of different anatomies or materials to locate boundaries in the first set among the different anatomies or materials, and 2) using at least one low mono-energetic diagnostic image for a second set of the different anatomies or materials to locate boundaries in the second set among the different anatomies or materials; and
determine a fractional flow reserve (FFR) index based on the 3-D anatomical model of coronary arteries; and
visually present the FFR index.

12. The non-transitory computer readable medium of claim 11, wherein the instructions cause the processor to process the spectral volumetric image data with a biophysical simulator component, which includes a spectral personalized feature extraction component and a spectral boundary condition parametric model component.

13. The non-transitory computer readable medium of claim 12, wherein the spectral personalized feature extraction component extracts features from the spectral 3-D anatomical model of the coronary arteries.

14. The non-transitory computer readable medium of claim 13, wherein the spectral boundary condition parametric model component determines spectral flow simulation boundary conditions from the extracted features.

15. The non-transitory computer readable medium of claim 14, wherein the biophysical simulator component further includes a flow simulator configured to determine the FFR index with the spectral flow simulation boundary conditions.

16. A method, comprising:
receiving spectral volumetric image data;
processing the spectral volumetric image data to segment a 3-D anatomical model of coronary arteries from the spectral volumetric image data by 1) using at least one high mono-energetic diagnostic image for a first set of different anatomies or materials to locate boundaries in the first set among the different anatomies or materials, and 2) using at least one low mono-energetic diagnostic image for a second set of the different anatomies or materials to locate boundaries in the second set among the different anatomies or materials; and
determining a fractional flow reserve (FFR) index based on the 3-D anatomical model of coronary arteries; and
visually presenting the FFR index.

17. The method of claim 16, further comprising:
extracting features from the spectral 3-D anatomical model; and
determining spectral boundary conditions from the extracted features for a flow simulation that determines the FFR index.

18. The method of claim 16, further comprising employing a spectrally enabled regularization over different spectral results or a materials domain.

19. The method of claim 16, further comprising locating a presence of anatomy of interest in a spectral image for the 3-D anatomical model of the coronary arteries.

* * * * *